United States Patent [19]

Frassica et al.

[11] Patent Number: 5,520,607
[45] Date of Patent: May 28, 1996

[54] HOLDING TRAY AND CLAMP ASSEMBLY FOR AN ENDOSCOPIC SHEATH

[75] Inventors: Jim Frassica, Chelmsford; Robert Ailinger, Norwood, both of Mass.; James P. Ryan, Amherst, N.H.

[73] Assignee: Vision Sciences, Inc., Natick, Mass.

[21] Appl. No.: 207,034

[22] Filed: Mar. 4, 1994

[51] Int. Cl.$^6$ ........................................................ A61B 1/00
[52] U.S. Cl. .............................. 600/102; 248/56; 248/80; 248/99
[58] Field of Search .............................. 128/4, 6; 433/49; 312/209; 248/50, 56, 58, 62, 75, 80, 95, 99; 269/329, 902, 909; 206/363, 438, 440, 69; 604/403; 600/101, 102

[56] References Cited

U.S. PATENT DOCUMENTS

| | | | |
|---|---|---|---|
| 4,907,395 | 3/1990 | Opie et al. | 53/434 |
| 4,997,084 | 3/1991 | Opie et al. | 206/364 |
| 5,325,846 | 6/1994 | Szabo | 128/4 |
| 5,337,731 | 8/1994 | Takahashi et al. | 128/4 |
| 5,349,941 | 9/1994 | Hori | 128/4 |

*Primary Examiner*—Richard J. Apley
*Assistant Examiner*—Beverly M. Flanagan
*Attorney, Agent, or Firm*—Seed and Berry

[57] ABSTRACT

A holding tray assembly for holding an endoscopic sheath during installation of the sheath onto an insertion tube of an endoscope and removal of the sheath from the insertion tube, wherein the sheath has a distal end and an open proximal end shaped to receive the insertion tube. The holding tray assembly has a tray with a slot formed therein extending inward from the peripheral edge of the tray. The slot is adapted to receive at least a portion of the endoscopic sheath so the proximal end of the sheath is positioned above the tray and the distal end of the sheath is below the tray. A sheath holding clamp is connected to the tray adjacent to a closed end of the slot, wherein the sheath holding clamp is adapted to releasably hold at least a portion of the endoscopic sheath within the slot. A tray securing apparatus is connected to the tray and is adapted to secure the tray onto a floor stand or other tray support structure. An endoscope holding assembly is connected to the tray to removably hold the endoscope during installation and removal of the endoscopic sheath. A bag removably surrounds and isolates the components of the holding tray assembly. At least a portion of the bag extends through the slot and is adapted to receive the sheath.

30 Claims, 5 Drawing Sheets

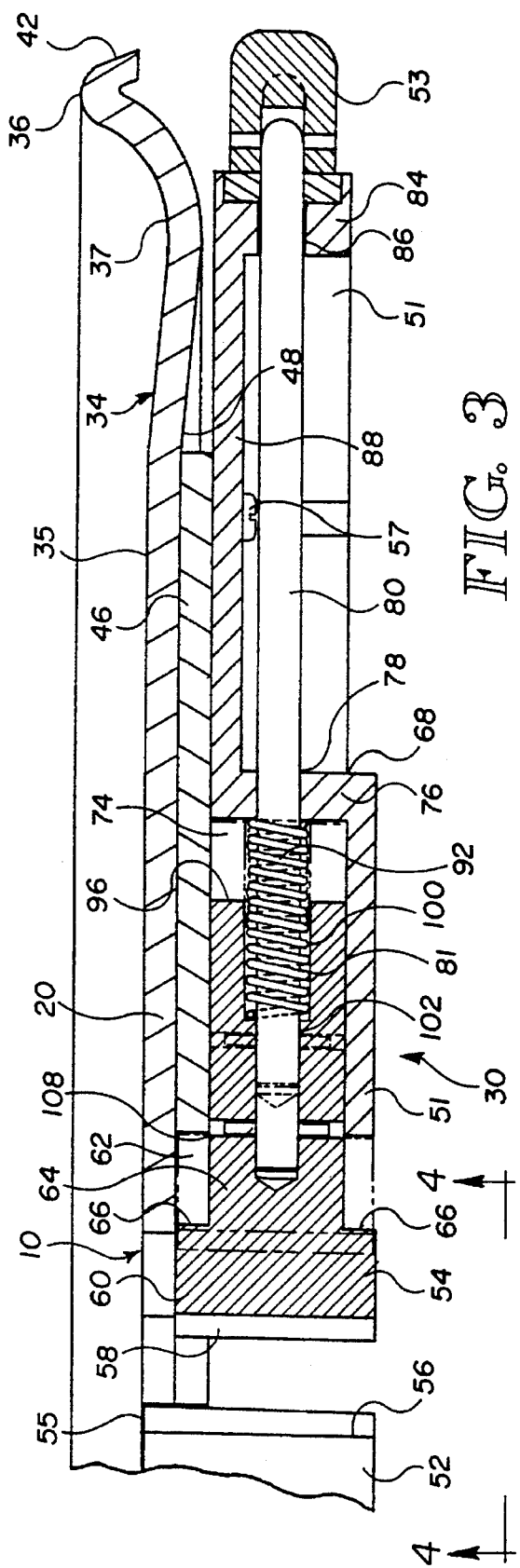
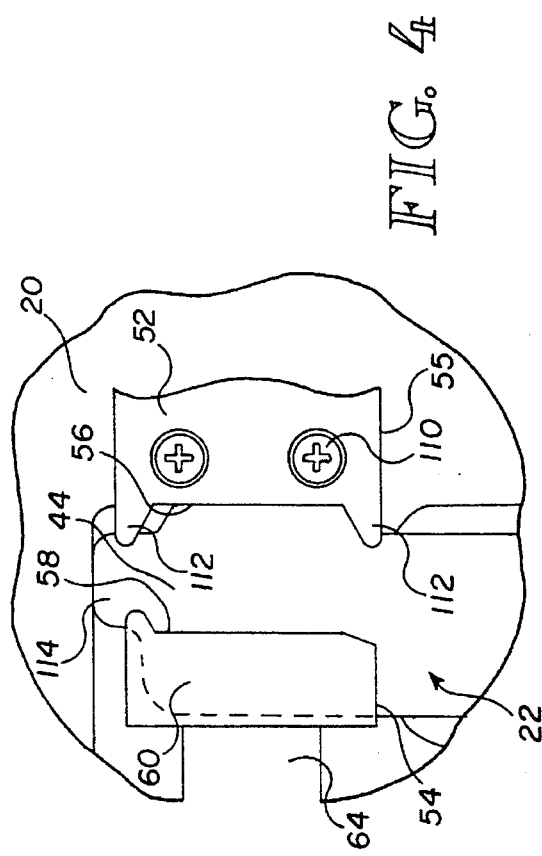
FIG. 3
FIG. 4

HOLDING TRAY AND CLAMP ASSEMBLY FOR AN ENDOSCOPIC SHEATH

TECHNICAL FIELD

This invention relates to the field of endoscopy, and more particularly, to an assembly for holding an endoscopic sheath during installation or removal of an endoscope.

BACKGROUND OF THE INVENTION

The use of endoscopes for diagnostic and therapeutic indications is rapidly expanding. To improve performance, endoscopes have been optimized to best accomplish their purpose. Accordingly, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes.

Instruments to examine the rectum and sigmoid; known as flexible sigmoidoscopes, are good examples of the usefulness of endoscopic technology. These devices are expensive, and they are used in a contaminated environment for a fairly brief procedure. There has been a large increase in the use of "flexible sigmoidoscopes " for use in screening symptomatic and asymptotic patients for colon and rectal cancer. Ideally, flexible sigmoidoscopes must be used rapidly and inexpensively in order to maintain the cost of such screening at acceptable levels. In order to achieve the ability to perform multiple endoscopic examinations in a short time period, disposable endoscopic sheaths are used to completely isolate the long insertion tube of the endoscope from contaminated exterior environments encountered during an endoscopic procedure.

However, physicians, nurses, and other personnel have experienced significant difficulties installing and removing the sheaths without contaminating themselves, equipment, or the patient. This contamination often occurs because the insertion tube of an endoscope is typically long, up to two meters long for a sigmoidoscopes, and very flexible. After a sheathed insertion tube is removed from a patient upon completing a portion of an endoscopic procedure, the contaminated sheath and insertion tube combination tend to flop about and contaminate equipment and personnel, such that the physician or nurse often must grab the assembly to control it while removing the sheath. In addition, the sheaths must be protected from becoming contaminated prior to use or during installation onto the insertion tube so they do not contaminate or infect patients during endoscopy, particularly those having a depressed immune system.

To reduce the risk of contamination during installation or removal of the sheath, stands have been used to receive the sheath during the installation and removal process, as shown in U.S. Pat. No. 4,907,395. However, the stands do not provide a work surface that allows the physician to set needed equipment or components in a convenient location, or that will hold or contain fluids or other material often used or encountered during the sheath's installation or removal procedure. In addition, the stand does not actually hold the sheath during installation or removal, rather it is adapted to hold a bag having a flange thereon that contains or receives the sheath. Thus, the stand does not provide a device to positively secure or hold the sheath during installation or removal.

As a result of the above-described risks of contamination, the difficulties experienced in installing and removing sheaths by conventional techniques, and the limitations in sheath holding devices, there has not heretofore been acceptable solutions to the problems of positively securing or holding the sheath for quick and easy installation or removal of the sheath while avoiding contamination and while providing a convenient work surface and containment area near the secured sheath.

SUMMARY OF THE INVENTION

Accordingly, it is an object of the present invention to provide a holding assembly for the installation and removal of a disposable endoscopic sheath that covers the insertion tube of an endoscope.

It is a further object of the present invention to provide a tray and clamp assembly adapted to securely and positively hold the sheath adjacent to a work surface that may be easily cleaned after use.

It is yet a further object of the invention to provide a tray and clamp assembly that allows for easy installation, removal, and disposal of the sheath in a sanitary manner and avoiding contamination of personnel, equipment, and the patient.

It is yet another object of the present invention to provide a tray and clamp assembly that allows a user to easily secure the sheath in a desired location or position prior to installation or removal of the insertion tube.

These and other objects of the invention are provided by a holding tray assembly that securely and removably holds an endoscopic sheath during installation of the sheath onto the insertion tube of an endoscope and during removal of the sheath from the insertion tube. In one embodiment of the invention, the holding tray assembly has a tray with an aperture formed therein that is sized to allow the insertion tube to extend through the aperture, and to receive at least a portion of the endoscopic sheath, such that the proximal end of the sheath is positioned above the tray and the distal end of the sheath is positioned below the tray. A sheath holding apparatus is connected to the tray adjacent to the aperture and adapted to releasably hold at least a portion of the endoscopic sheath within the aperture. The holding tray assembly further has a tray securing apparatus that is connected to the tray and adapted to secure the tray onto a tray assembly support structure, such as a floor stand, workbench, or the like.

In a preferred embodiment of the invention, the holding tray assembly includes a tray having a slot formed therein that extends from a peripheral edge of the tray to an end portion of the slot that is adjacent to the sheath holding apparatus. The slot is provided with a sufficient width so the sheath, with or without the insertion tube inserted, can be easily loaded into the holding tray assembly from the side of the tray and clamped in a desired position. The sheath holding apparatus is preferably a clamp adapted to removably secure a portion of the sheath within the slot during installation or removal of the sheath.

The tray preferably has a substantially flat work surface with a raised lip around the perimeter to form a pan-like structure that is adapted to contain material or liquids thereon. The tray also may be reinforced by a reinforcing plate mounted to the bottom surface of the tray to provide a rigid work surface. The holding tray assembly further has an endoscope holding unit connected to the tray and adapted to removably hold the endoscope during installation and removal of the sheath.

In one embodiment of the present invention, the holding tray assembly has a cover removably surrounding the tray and sheath holding apparatus to isolate the tray and the sheath holding apparatus from contaminants. The cover is shaped and sized to receive the sheath and to at least partially extend through the slot in a position so the sheath can be securely held in position by the sheath holding apparatus.

Further objects and advantages of the subject invention will become apparent when the following detailed description of the preferred embodiment taken in conjunction with the drawings.

BRIEF DESCRIPTION OF THE DRAWINGS

FIG. 3 is a cross-sectional, view taken along line 3—3 of FIG. 2.

FIG. 4 is an enlarged bottom plan view of the clamping jaws of FIG. 3.

DETAILED DESCRIPTION OF THE INVENTION

Figure 1:
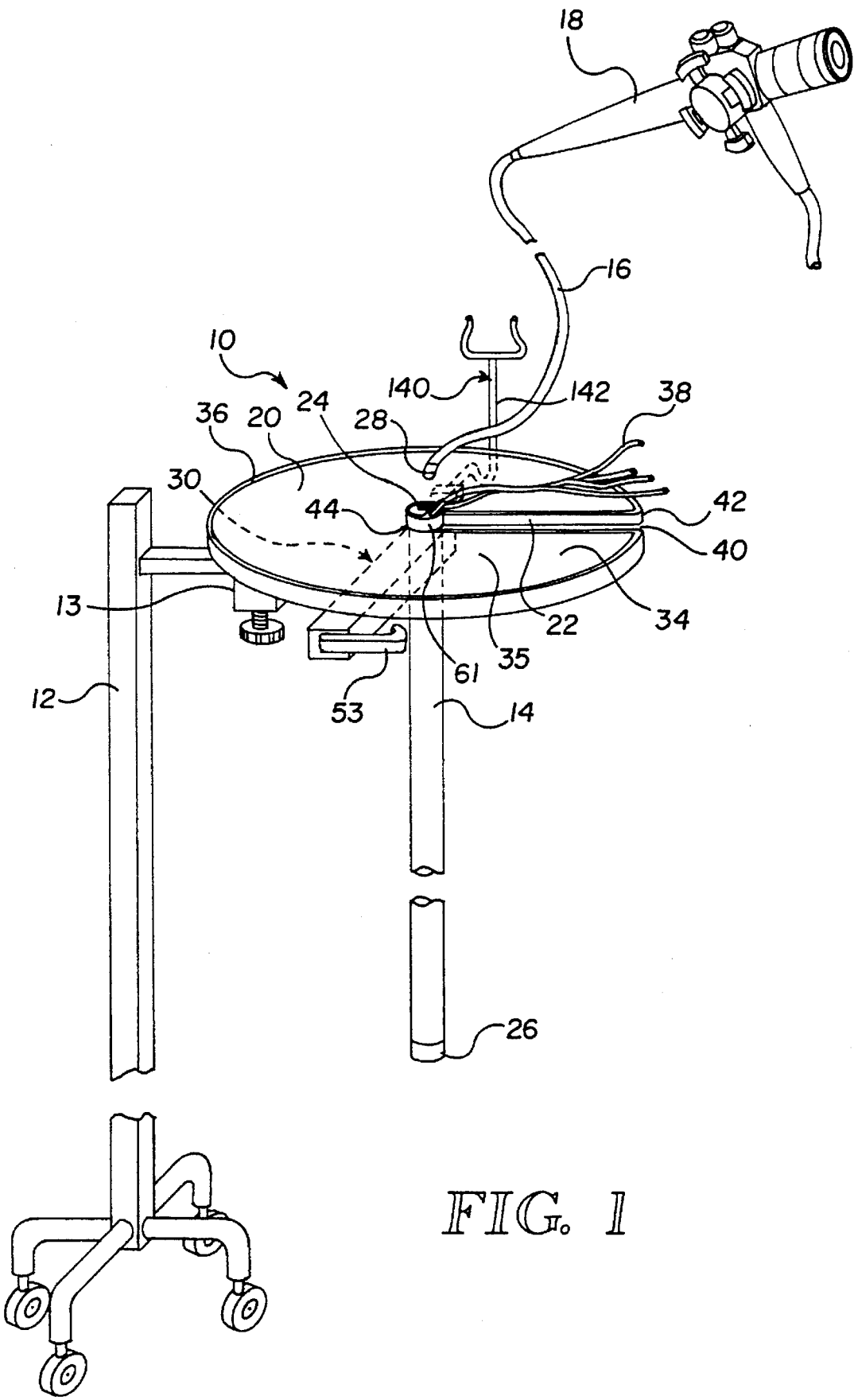
FIG. 1 is a schematic isometric view of a holding tray assembly in accordance with the present invention with an endoscopic sheath secured in position for installation or removal of an endoscope.

As shown in FIG. 1, a holding tray assembly 10, in accordance with the present invention, mounts to a stand 12 or other suitable tray support structure with a tray securing device, such as a tray clamp 13, and is adapted to securely hold an endoscopic sheath 14 in a easily accessible position during installation of the sheath onto, or removal of the sheath from a flexible, elongated insertion tube 16 of an endoscope 18. The tray clamp 13 is connected to the tray near a peripheral edge and is adapted to secure the tray onto the stand 12 at a desired height to facilitate the installation or removal of the sheath. The assembly 10 further has a tray 20 that provides a substantially flat work surface. The tray 20 has a slot 22 or other suitable aperture formed therein that is sized to receive at least a portion of the sheath 14 and to allow the insertion tube 16 to extend through the slot. As such, the proximal end 24 of the sheath is positioned above the tray and the distal end 26 of the sheath is positioned below the tray.

A clamp 30 or other sheath holding apparatus is connected to the tray 20 adjacent to a portion of the slot 22. The clamp 30 is adapted to releasably hold at least a portion of the sheath 14 within the slot so the proximal and distal ends 24 and 26 are above and below the slot, respectively, In this position, the insertion tube 16 can be inserted into the sheath 14 by placing the distal end 28 of the insertion tube into the open proximal end 24 of the sheath and extending the insertion tube along the length of the sheath until the distal end of the insertion tube properly communicates with the distal end 26 of the sheath. Conversely, the insertion tube 16 can be removed from the sheath by reversing the above installation procedure and withdrawing the insertion tube through the open proximal end 24 of the sheath.

Figure 2:
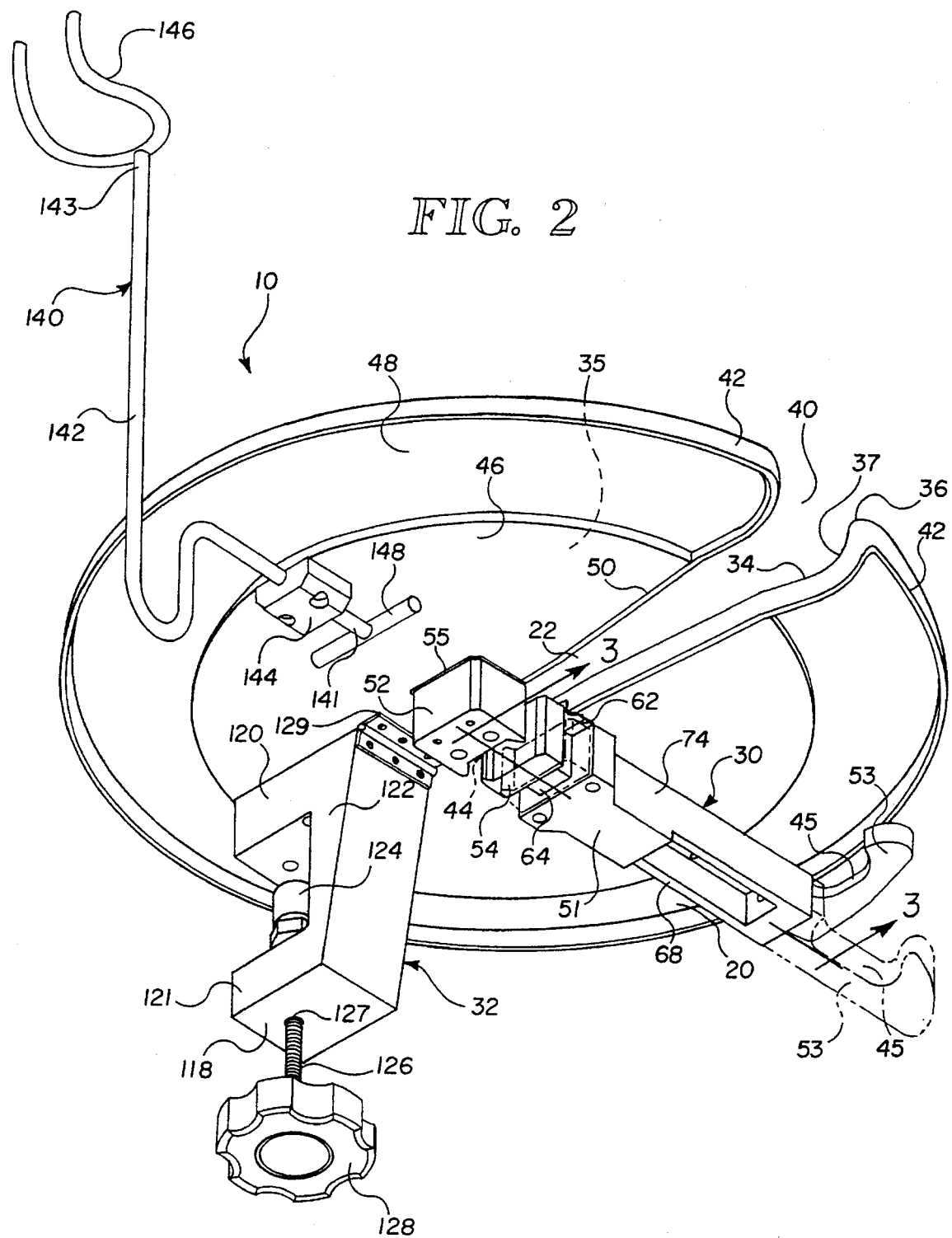
FIG. 2 is an enlarged bottom isometric view of the holding tray assembly of FIG. 1 with the endoscopic sheath and stand removed and an endoscope holding unit shown.

As best seen in FIGS. 1 and 2, the tray 20 of the preferred embodiment is a substantially circular tray having a top surface 34 that provides a work surface and a raised lip 36 or the like around the perimeter of the tray. The top surface 34 has a substantially flat middle portion 35 and a concave outer portion 37 that dips below the middle portion to form a channel area into which fluid or liquids will collect and be contained. Thus, the middle portion 35, outer portion 37, and lip 36 form a shallow, pan-like structure that will contain items or other material placed on the tray. For example, the tray 20 can support, in a convenient, close position, equipment or tools used during the endoscopic procedure or portions of the endoscopic assembly, such as air and water channels 38 that extend into the sheath 14. In addition, the raised lip 36 and concave outer portion 37 help to contain other material or fluids that result from an endoscopic procedure, thereby reducing the risk of the material or fluids contaminating other equipment or personnel.

In the preferred embodiment, the tray 20 is made of a non-porous material, such as an acrylic and ABS composite material, that provides a strong, chemically resistant, cleanable surface. Other non-porous materials such as plastic and acrylic composites, aluminum, or other metals can also be used to provide a strong, chemically resistant, cleanable surface.

In the preferred embodiment, the slot 22 extends from an open end 40 along the peripheral edge 42 of the tray 20 to a closed end 44 near the center of the tray. The open end 40 is positioned opposite the tray clamp 13 so the stand 12 will not interfere with access to the slot 22 as the sheath 14 is moved into or out of the slot. Accordingly, the assembly 10 allows a physician or nurse to move the sheath 14, with or without the insertion tube 16 installed, into or our of the slot and clamp 30 from the side of the tray 20 while the sheath freely hangs vertically with the distal end 26 closest to the floor. This arrangement greatly reduces the risk of contaminating equipment, personnel, or the patient. For example, when a sheathed insertion tube is removed after performing an endoscopic procedure, the exterior portion of the sheath is grossly contaminated with bodily fluids, stool, mucous, and the like. The tray 20 and slot 22 arrangement allows the physician to hang the sheathed insertion tube vertically so it will not flop around while being moved through the slot and secured in the clamp 30. Once the sheath 14 is clamped, the insertion tube 16 can be removed from the contaminated sheath 14 in a slow and controlled manner.

As best seen in FIG. 2, the tray 20 has a reinforcing plate 46 mounted to a bottom surface 48 of the tray, wherein the reinforcing plate 46 has a slot 50 or other suitable aperture that corresponds to the slot 22 of the tray 20. As such, the reinforcing plate 46 does not cause any interference with the sheath as it is moved along the length of the slots 22 and 50 to the closed end 44 and secured in the clamp 30. The reinforcing plate 46 is made of a rigid material that provides additional structural rigidity to the tray 20 so that the peripheral edges 42 of the tray near the open end 40 of the slot 22 will not bend or be displaced when equipment, tools, or other material is placed on the tray near the open end of the slot. In the preferred embodiment, the reinforcing plate 46 is a rigid composite or metal plate secured to the bottom of the tray with conventional fasteners.

Referring to in FIGS. 2 and 3, the clamp 30 is mounted to the bottom of the tray 20 and engages a portion of the reinforcing plate 46. The clamp 30 has a clamp housing 51 fastened with conventional fastener 57 to the tray 20 and reinforcing plate 46. The clamp housing 51 extends from the peripheral edge 42 to a position radially outward from the end 44 of the slot 22. The clamp 30 further has a handle 53 that is coupled to at least one of two clamping jaws 52 and 54 located adjacent to the end 44 of the slot 22. The handle 53 is located radially outward from the peripheral edge 42 of the tray 20, thereby providing easy access to the handle from virtually any position. The handle 53 has a cutout area 45 that is shaped to form a grip or the like that a physician or nurse can grasp while pivoting the handle between an open released position, shown in phantom, and a closed clamped position.

The clamping jaws 52 and 54 are located on opposite sides of the slot 22. In the preferred embodiment, the first clamping jaw 52 is a stationary jaw secured to the tray 20 within a cutout area 55 in the reinforcing plate 46. The second clamping jaw 54 is a movable clamping jaw that is coupled to the handle 53 and adapted to move between an open released position, shown in phantom in FIG. 2, and a closed clamped position. When the movable jaw 54 is in the open released position, the distance between the stationary jaw 52 and movable jaw is maximized. Conversely, when the movable jaw 54 is in the closed clamped position, the distance between the jaws is minimized. In the closed clamped position, the distance between the jaws 52 and 54 is small enough so the jaws engage and securely hold the sheath 14 within the slot 22 such that pushing and pulling forces can be exerted on the sheath during the installation or removal procedure without displacing the sheath from the clamp 30.

As shown in FIG. 3, the movable clamping jaw 54 has a head portion 60, a body portion 64 connected to one side of the head portion, and a clamping face 58 on the opposite side of the head portion. The stationary jaw 52 also has a clamping face 56. The clamping faces are shaped so as to match a draft angle of a generally rigid clamp interface body 61 of the sheath, illustrated in FIG. 1, to assure that the jaws fully engage the sheath. The clamping faces 56 and 58 are substantially perpendicularly oriented to the tray 20 and aligned with the edges of the slot 22 to achieve the maximum holding forces while aligning the sheath 14 within the slot.

In addition, it is desirable to position the jaws 52 and 54 as close to the tray and slot as possible to limit bending of the sheath within the slot during installation or removal of the sheath. Accordingly, the reinforcing plate 46 has a cutout area 62 that is immediately adjacent to the slot 22 and adapted to receive the head portion 60 of the movable jaw. Thus, the head portion 60 slides along the bottom surface 48 of the tray 22 within the cutout area 62 as the movable jaw moves between the open and closed positions.

A shoulder portion 66 is formed at the intersection of the head and body portions 60 and 64. The shoulder portion 66 is adapted to engage the clamp housing 51 and block the movable jaw 54 from moving beyond a set position when the head and body portions 60 and 64 move to the open released position. The body portion 64 is received in a receiving area 68 of the clamp housing 51. The receiving area 68 has a cross section that is slightly larger than the cross section of the body portion 64, so the body portion will slide within the receiving area as the movable jaw 54 moves between the open released position and the closed clamped position.

The receiving area 68 is formed by a bottom panel 72 that is parallel to the reinforcing plate 46 and two side panels 74 perpendicular to the reinforcing plate and a back panel 76 that closes out the back side of the receiving area. As such, the reinforcing plate 46 acts as a top close-out panel of the receiving area 68. The back panel 76 has a bore 78 formed therein that is adapted to slidably engage a rod 80 which connects at one end to the body portion 64 within the receiving area 68. The body portion 64 has a stepped axial bore 81 formed therein which extends from the back end 96 of the body member to a terminating position 98 at a predetermined position along the length of the body portion. The stepped bore 81 is coaxially aligned with the longitudinal axis of the body portion 64 and adapted to receive the rod 80.

The rod 80 extends along the length of the housing 51 and connects at its opposite end to the handle 53. The handle 53 is connected to the rod 80 in such a manner that, when the handle is moved or pivoted between an open position, shown in phantom in FIG. 2, and a closed position, the rod will move axially along the longitudinal axis of the clamp housing 51. This axial movement of the rod 80 slides the body portion 64 of the movable jaw 54 within the receiving area 68, thereby causing the head portion 60 and clamping face 58 to move between the open and closed positions.

A spring 92 or other biasing member positioned within the receiving area 68 biases the movable clamping jaw 54 to the closed clamped position. The spring 92 is a coil spring that is mounted on the rod 80 and extends partially into the stepped axial bore 81. The stepped axial bore 81 has a first portion 100 located closer to the back end 96 of the body portion 64 and a second portion 102 that is closer to the head member 60. The first portion 100 has a diameter that is greater than the diameter of the second portion 102, such that a shoulder 104 is formed at the intersection of the two portions. The spring 92 has an outer diameter that is greater than the diameter of the second portion 102 of the bore 81 and less than the diameter of the first portion 100 so one end of the spring abuts the shoulder 104. The opposite end of the spring 92 has an outer diameter that is larger than the diameter of the axial bore 78 in the back panel 76 of the receiving area 68, such that the spring abuts the back panel and is retained within the receiving area 68. In the preferred embodiment, the spring 92 is in a partially compressed state when the movable jaw 54 is in the closed clamped position so a positive biasing force acts on the movable jaw throughout its full range of motion.

Accordingly, when the handle 53 is pivoted and the rod 80 moves axially, the movable clamping jaw 54 slides to the open released position, wherein the head portion 60 slides into and fills the cutout portion 62 and the shoulder 66 abuts the clamp housing 51 and blocks the head portion 60 from sliding past a predetermined position.

As best seen in FIG. 4, the stationary clamping jaw 52 is connected to the bottom of the tray 20 within the cutout 55 by conventional fasteners 110. The stationary jaw 52 has protrusions 112 that extend into the slot area and act to align an endoscopic sheath (not shown) and to prevent the sheath from sliding out of the jaws during installation or removal of the sheath onto or from the insertion tube. As indicated above, the head portion 60 of the movable jaw 54 is positioned adjacent to the edge of the slot 22 opposite the stationary clamping jaw 52, such that the head portion 60 extends into the slot area when the movable jaw is in the closed clamped position. A notch 114 or other suitable clearance area is formed in the tray 20 at the closed end 44 of the slot 22 and is located so the head portion 60 does not cover the notch when the movable jaw 54 is in the closed position. The notch 114 is sized and shaped to receive excess material of a loose sheath or a protective bag or cover that receives the sheath, as discussed in greater detail below, so the sheath or bag material will not be damaged by binding against the clamp faces 56 and 58.

Referring back to FIG. 2, the tray clamp 13 is fastened to the reinforcing plate 46 on the bottom surface of the tray 20. In the preferred embodiment, the tray clamp 13 is a C-clamp having a body 118 with a vertical leg 122, one horizontal leg 120 that engages the reinforcing plate 46, a second horizontal leg 121 below the first leg, and an open area of the C-shaped body facing toward the peripheral edge 42 of the tray 20. The tray clamp 13 further has an adjustable foot 124 that can be tightened to releasably engage an edge of a table top, workbench, or floor stand, thereby applying a sufficient clamping force to securely attach the holding tray assembly 10 to the tray support structure.

The adjustable foot 124 is connected to one end of a threaded shaft 126 that extends through a threaded bore 127 in the second horizontal leg 121. An adjustment knob 128 connects to the opposite end of the shaft 126, whereby rotation of the adjustment knob about the longitudinal axis of the shaft 126 causes the adjustable foot to move within the open area of the C-shaped body 118. Accordingly, the tray clamp 13 can be easily and removably secured to a wide variety of tray support structures.

In one embodiment of the present invention, the tray clamp 13 is pivotally connected to the holding tray 20 or the reinforcing plate 46 with a hinge mechanism 129 or the like. This hinged tray clamp is adapted to allow the holding tray 20 to be moved between a substantially horizontal, working position, as shown in FIG. 2, and a substantially vertical, stored position. Thus, the holding tray assembly 10 can be pivoted to the vertical stored position when it is not being used and additional space is desired before, during, or after an endoscopic procedure.

Figure 5:
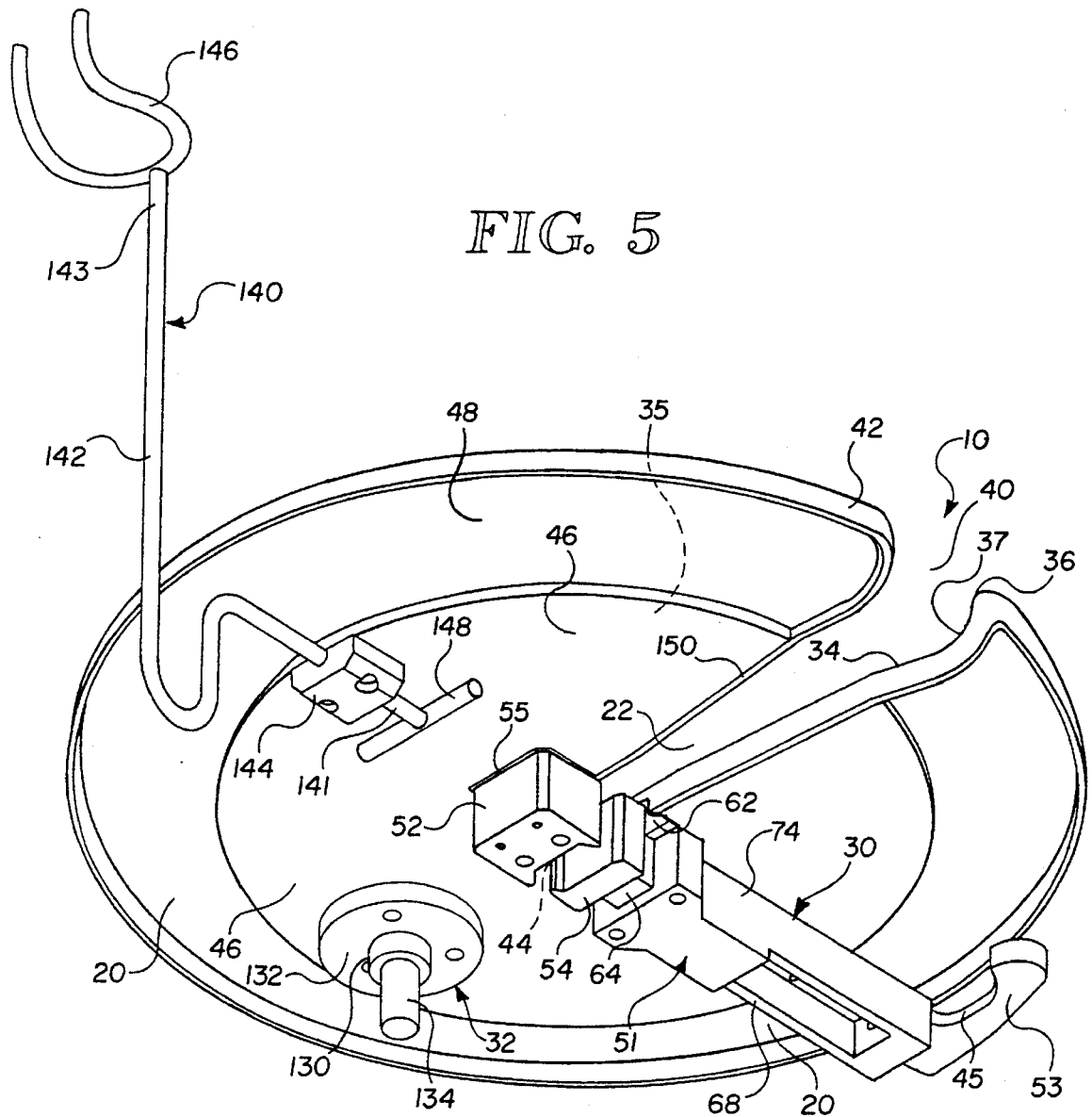
FIG. 5 is a bottom isometric view of an alternate embodiment of the present invention with a pin assembly mounted to the tray in an offset position.

In an alternate embodiment of the present invention, as best seen in FIG. 5, the holding tray assembly 10 has a pin assembly 130 as an alternate tray securing device. The pin assembly 130 has a base portion 132 connected to the reinforcing plate 46, and a pin portion 134 or shaft connected to the base portion. The base portion 132 can also connect directly to the tray 20 if, for example, a reinforcing plate is not used by the holding tray assembly. The pin 134 is substantially perpendicular to the base portion and is sized to fit into a pin receiving aperture on a floor stand 135 or other tray support structure, shown in FIG. 6. Thus, the pin portion 134 will pivotally engage the pin receiving area, so the holding tray assembly 10 is securely held in a substantially horizontal position.

The pin assembly 130, in the preferred alternate embodiment, is mounted to the reinforcing plate 46 in an offset position between the center portion of the tray and the peripheral edge 42. In this offset position, the tray assembly can be pivoted about the pin 134 to a plurality of positions. Accordingly, this offset pin arrangement allows the physician or nurse to pivot the tray 20 out of the way without having to move the floor stand when additional space is needed before, during, or after the endoscopic procedure.

As best seen in FIGS. 1 and 2, the holding tray assembly 10 of the preferred embodiment further has an endoscope holding assembly 140 coupled to the tray 20. The holding assembly 140 is shaped and sized to removably hold the endoscope 18, for example, during installation and removal of the sheath 14. In the preferred embodiment, the endoscope holding assembly 140 is a curved rod member 142 that is fastened at a bottom end 141 to the bottom of the reinforcing plate 46 by a fastening block 144. A blocking member 148 is connected to the bottom end 141 and it engages the reinforcing plate 46 to prevent the rod 142 from pivoting within the fastening block 144. The rod 142 extends horizontally from the bottom of the reinforcing plate 46 beyond the peripheral edge 42 of the tray 20, wherein the rod 142 is bent so it extends vertically upward above the tray. The top portion 143 of the rod 142 connects to an endoscope seat portion 146 that is adapted to removably receive the endoscope 18. As such, a physician or nurse can place the endoscope into the seat portion 146 of the endoscope holding assembly 140 during removal of a contaminated sheath or during installation of a new sheath without having to lay the endoscope down onto a potentially contaminated surface.

Figure 6:
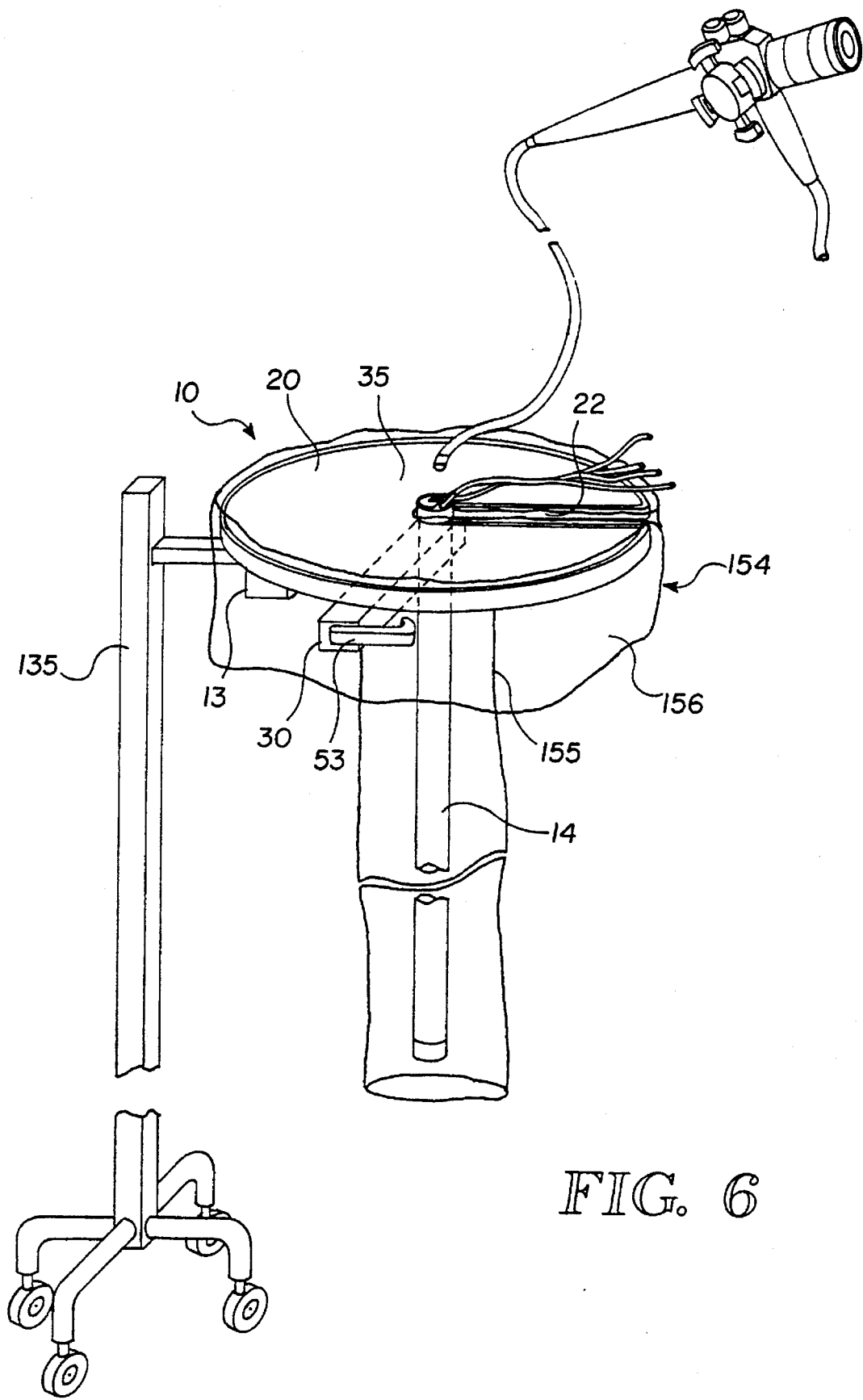
FIG. 6 is a top isometric view of the holding tray assembly of FIG. 1 with a cover installed and clamp and a sheath positioned within the cover.

As best seen in FIG. 6, the holding tray assembly 10 further includes a bag 154 or other suitable cover that drapes the tray 20 to isolate the tray 20, clamp 30, and other components from contaminants that may be encountered during an endoscopic procedure. When the bag 154 is installed around the components, at least a portion 155 of the bag 154 is positioned within the slot 22 and is adapted to receive at least a portion of the endoscopic sheath 14. In the preferred embodiment, the bag 154 is made of a transparent, pliable material that will loosely conform to the shape of the tray. With the bag 154 installed, the physician or nurse can still grasp and pivot the handle 53 of the clamp 30 so as to move the clamp between the open released position and the closed clamped position. As such, the handle 53 is made with a smooth surface and rounded edges to avoid puncturing or damaging the bag 154.

In the preferred embodiment, the bag 154 has a T-shape whereby the top portion of the bag covers the tray 20 and the bottom portion 155 extends through the slot and is shaped to receive and cover a sheath positioned in the holding assembly 10. As indicated above, when the bag 154 is installed and a sheath 14 is secured in the clamp 30, the notch 114 at the closed end 44 of the slot 22, as seen in FIG. 4, receives any excess bag material near the clamp and around the sheath. Accordingly, the notch 114 helps to prevent the bag 154 from bunching up between the sheath 14 and the clamping jaws 52 and 54, thereby reducing the risk of damaging the bag or the sheath.

Referring again to FIGS. 1 and 2, the holding tray assembly 10 is used during the method of installing the sheath 14 onto the insertion tube 16 of the endoscope 18 and for removing the sheath from the insertion tube. In the preferred embodiment, the holding tray assembly 10 mounted on the floor stand 12 is positioned in a desired position, for example, adjacent to an examination table. The sheath 14 is inserted into the slot 22 or aperture so the open proximal end 24 of the sheath is adjacent to the slot 22. The sheath 14 is removably secured by the clamp 30 in an operable position so the sheath's open proximal end 24 is positioned above the tray, the distal end 26 is below the tray, and a portion of the sheath extends through the slot. Once the sheath 14 is secured in this position, the insertion tube 16 of the endoscope 18 is installed into the sheath 14, thereby forming a sheathed endoscope unit. In this position, the air and water channels 38 can be connected to their respective air and water source, visual imaging systems of the endoscope can be connected, and other preparatory connections or adjustments can be made to the sheathed endoscope unit.

The clamp 30 is then opened and the sheathed endoscope unit is removed from the holding tray assembly 10 through the slot 22 and the opening 40. A desired endoscopic procedure is performed with the sheathed endoscope unit, and then the unit is placed back into the holding tray assembly 10 and removably secured therein with the clamp 30. The sheath 14 is then disconnected from other equipment or connections as necessary and the insertion tube is removed from the sheath. The sheath 14, which is typically very contaminated after the endoscopic procedure, is then removed from the clamp 30 and disposed of in a suitable receptacle.

In an alternate method of using the holding tray assembly, the bag 154, shown in FIG. 6, is placed over the tray 20, clamp 30, and other components so at least a portion of the cover extends through the slot 22 adjacent to the clamp 30. The sheath 14 is inserted into the bag 154 within the slot 22 and secured in place by the clamp 30. Then the sheath is installed and the sheathed endoscope unit is used to perform an endoscopic procedure. After the endoscopic procedure, the endoscopic unit is placed back into the slot 22, within the bag 154 and the insertion tube is removed from the sheath. Thereafter, the sheath 14 is released from the clamp 30 and the bag 154 containing the sheath is removed from the holding assembly 10 as a unit. Thereafter, the bag 154 and sheath 14 can be disposed of in a suitable receptacle.

Numerous modifications and variations of the holding tray and clamp assembly for an endoscopic sheath disclosed herein will occur to those skilled in the art in view of this disclosure. For example, the clamp assembly can be adapted to be controlled from a remote location, or the tray clamp can be adapted to allow the tray to slide laterally between a stored position and an active position. Therefore, it is to be understood that the modifications and variations, and equivalents thereof, may be practiced while remaining within the spirit and scope of the invention as defined by the following claims.

We claim:

1. A holding tray assembly for holding an endoscopic sheath during installation of the sheath onto an insertion tube of an endoscope and removal of the sheath from the insertion tube, wherein the sheath has a distal end and an open proximal end shaped to receive the insertion tube, comprising:

a tray having a aperture formed therein, said aperture sized to receive at least a portion of the endoscopic sheath and to allow the insertion tube to extend through said aperture with the proximal end of said sheath positioned above said tray and the distal end of said sheath positioned below said tray;

a sheath holding apparatus connected to said tray adjacent to said aperture, said holding apparatus being adapted to releasably hold at least a portion of the endoscopic sheath within said aperture; and a tray securing apparatus connected to said tray and adapted to secure said tray onto a tray support structure.

2. The holding tray assembly of claim 1 wherein said aperture is a slot extending from a peripheral edge of said tray to an end of said slot adjacent to said sheath holding apparatus, said slot having a sufficient width to receive said sheath so that said sheath can be loaded into said aperture from the side of said tray.

3. The holding tray assembly of claim 1 wherein said tray has a substantially flat work surface having a perimeter and a raised lip around said perimeter to form a tray adapted to contain material thereon.

4. The holding tray assembly of claim 1 wherein said tray has a top surface, a bottom surface, and a reinforcing plate mounted to said bottom surface.

5. The holding tray assembly of claim 4 wherein said reinforcing plate has an aperture located in a position corresponding to said aperture in said tray.

6. The holding tray assembly of claim 1 wherein said tray is made of a non-porous material.

7. The holding tray assembly of claim 1 wherein said tray is an acrylic and plastic composite.

8. The holding tray assembly of claim 1 wherein said tray is metal.

9. The holding tray assembly of claim 1 wherein said sheath holding apparatus is a clamp assembly.

10. The holding tray assembly of claim 9 wherein said clamp assembly has at least one movable clamping jaw adapted to move between an open release position and a closed clamping position, said movable clamping jaw being biased to said closed clamping position.

11. The holding tray assembly of claim 10 wherein said movable clamping jaw is biased by a spring.

12. The holding tray assembly of claim 9 wherein said clamping assembly further comprises a handle mechanism coupled to said movable clamping jaw and adapted to move said jaw between said open and closed positions.

13. The holding tray assembly of claim 1 wherein said tray securing apparatus is a clamp adapted to removably secure said holding tray assembly to a support structure.

14. The holding tray assembly of claim 1 wherein said tray securing apparatus is a pin assembly adapted to pivotally fit in a pin receiving area mounted on a tray support structure.

15. The holding tray assembly of claim 14 wherein said pin assembly is attached to said tray at a position offset from the center of said tray so said holding tray assembly can be pivoted to a plurality of positions relative to the tray support structure.

16. The holding tray assembly of claim 1 wherein said tray securing apparatus is movably connected to said holding tray and adapted so said holding tray can be moved between a substantially horizontal working position and a substantially vertical stored position.

17. The holding tray assembly of claim 1 further comprising a cover removably connected to said tray so as to substantially surround said tray, at least a portion of said cover being positioned in said aperture and being adapted to receive at least a portion of said endoscopic sheath.

18. The holding tray assembly of claim 17 wherein said removable cover assembly is a bag.

19. The holding tray assembly of claim 17 wherein said aperture in said tray has a clearance area adapted to receive excess cover material located within said aperture.

20. The holding tray assembly of claim 18 wherein said bag is a T-shaped bag having a narrow portion and a wide portion, said narrow portion being adapted to be positioned in said aperture and to receive at least a portion of said endoscopic sheath, and said wide portion being adapted to substantially cover said tray.

21. The holding tray assembly of claim 1, further comprising an endoscope holding assembly coupled to said tray, said holding assembly being shaped and sized to removably hold the endoscope during installation and removal of the endoscopic sheath.

22. A holding tray assembly for holding an endoscopic sheath during installation of the sheath onto an insertion tube of an endoscope and removal of the sheath from the insertion tube, wherein the sheath has a distal end and an open proximal end shaped to receive the insertion tube, comprising:

a tray having an aperture therein;

a sheath holding apparatus connected to said tray adjacent to said aperture, said holding apparatus being adapted to releasably hold the open proximal end of the sheath adjacent to said aperture;

a tray securing assembly connected to said tray and adapted to secure said tray onto a tray support structure;

an endoscope holding assembly coupled to said tray and adapted to removably hold the endoscope during installation and removal of the endoscopic sheath; and a cover removably surrounding said tray, said cover at least partially extending through said aperture.

23. The holding tray assembly of claim 22 wherein said aperture is a slot extending from a peripheral edge of said tray to an end of said slot adjacent to said sheath holding apparatus, said slot having a sufficient width to receive said sheath so that said sheath can be loaded into said aperture from the side of said tray.

24. The holding tray assembly of claim 22 wherein said tray has a reinforcing plate connected thereto.

25. The holding tray assembly of claim 23 wherein said tray has a substantially flat work surface having a perimeter and a raised lip around said perimeter to form a tray adapted to contain material thereon.

26. A method for installing an endoscopic sheath onto an insertion tube of an endoscope and for removing the endoscopic sheath from the insertion tube, the endoscopic sheath having a distal end and an open proximal end adapted to receive at least a portion of the insertion tube, comprising the steps of:

positioning a tray device mounted on a support structure in a desired position, wherein the tray has an aperture adapted to receive at least a portion of the endoscopic sheath;

inserting at least a portion of the endoscopic sheath into the aperture so the open proximal end of the endoscopic sheath is adjacent to the aperture;

removably securing the sheath in an operable position with a securing mechanism to hold the sheath so at least a portion of the sheath extends through the aperture slot and so the open proximal end is above the tray device;

installing the insertion tube of the endoscope in the sheath, thereby forming a sheathed endoscope unit;

removing the sheathed endoscope unit from the tray;

performing a procedure with the sheathed endoscopic unit;

placing the sheathed endoscopic unit into tray so the sheath is removably secured by the securing mechanism; and removing the insertion tube from the sheath.

27. The method of claim 26 wherein said step of removably securing said sheath in an operable position comprises clamping said sheath in the operable position with a clamp mechanism coupled to the tray.

28. The method of claim 26 further comprising the steps of removing the sheath from the tray device.

29. The method of claim 26 further comprising the step of covering said tray with a cover so at least a portion of the cover means extends through the aperture adjacent to the securing mechanism.

30. The method of claim 29 further comprising the step of removing the cover from the tray device.

* * * * *